United States Patent [19]

Lundak

[11] Patent Number: 4,594,325
[45] Date of Patent: Jun. 10, 1986

[54] HIGH FUSION FREQUENCY FUSIBLE LYMPHOBLASTOID CELL LINE

[75] Inventor: Robert L. Lundak, Riverside, Calif.

[73] Assignee: The Regents of the University of Calif., Berkeley, Calif.

[21] Appl. No.: 247,656

[22] Filed: Mar. 26, 1981

[51] Int. Cl.[4] .................. C12N 5/00; C12N 15/00; C12R 1/91
[52] U.S. Cl. ................... 435/240; 435/172.2; 435/948; 935/100
[58] Field of Search .............. 435/240, 241, 243, 244, 435/172; 424/85, 86, 87

[56] References Cited

PUBLICATIONS

Levy et al., "Further Characteraction of the W1-L2 and W1-L1 Lymphoblastoid Lines", *Journal of the National Cancer Institute*, vol. 46 (1971), pp. 647–652.
Croce et al., "Production of Human Hybridomas Secreting Antibodies to Measles Virus" *Nature*, vol. 288 (Dec. 4, 1980), pp. 488–489.
Ham et al., "Media and Growth Requirements" *Methods in Enzymology*, vol. 58 (1979), pp. 77–79, 90–93.
Iscove et al., "Complete Replacement of Serum by Albumin, Transferrin, and Soybean Lipid in Cultures of Lipopolysaccharide-Reactive B Lymphocyete, *Journal of Experimental Medicine* 147:(1978), pp. 923–933.
Kohler et al., "Derivation of Specific Antibody-Producing Tissue Culture and Tumor Lines by Cell Fusion," *European Journal of Immunology*, vol. 6 (1976), pp. 511–519.
Litwin, "A Survey of Various Media and Growth Factors used in Cell Cultivation," *Developments in Biological Standards*, vol. 42 (1979), pp. 37–45.

*Primary Examiner*—Thomas G. Wiseman
*Assistant Examiner*—John Edward Tarcza
*Attorney, Agent, or Firm*—Bertram I. Rowland

[57] ABSTRACT

Human lymphoblastoid cell line capable of acting as a fusion partner in the preparation of hybridomas is grown and selected under conditions whereby a cell line is obtained having greatly enhanced fusion efficiency over the parent cell line. The cell line is derived from UC 729 by growing in Iscove's modified serum-free medium with plating at relatively high densities, followed by cloning at limiting dilutions and selecting for high frequency fusion.

The subject cell line referred to as WI-L2-729 $HF_2$ has the A.T.C.C. designation number CRL 8062, having been deposited on Apr. 2, 1981.

2 Claims, No Drawings

HIGH FUSION FREQUENCY FUSIBLE LYMPHOBLASTOID CELL LINE

BACKGROUND OF THE INVENTION

1. Field of the Invention

The mammalian immune system provides one of the major defense mechanisms against disease. It has also for a long time been the sole source of antibodies. These molecules are almost uniquely capable of binding to a specific structural element of an organic compound. By virtue of this ability antisera have found increasing use in diagnostics. The antisera prepared by immunizing an animal is a heterogeneous mixture with a broad range of binding ability. Where antigens are involved, having a plurality of determinant sites, the antiserum which forms will have antibodies binding to the various determinant sites. In addition, the antisera which are normally isolated from serum will have a major proportion of antibodies unrelated to the immunogen of interest.

The recent discovery of Kohler and Milstein, Nature (1975), 256, 495–497, led the way in preparing monoclonal antibodies. These antibodies are homogeneous compositions having uniform affinity for a binding site, although there can be some contamination of light or heavy chain from the fusion partner.

The Kohler and Milstein work was limited to mouse antibodies. Subsequently, in 1980, the ability to cross human cells to produce hybridomas capable of excreting human antibodies was reported by two different groups. Having shown that human antibodies can be produced by human hybridomas, many improvements in the ability to produce antibodies may now be forthcoming.

In producing antibodies from human hybridomas, there are many considerations. One consideration is the degree to which the fusion partner—the immortalized cell—produces light or heavy chains or other immunoglobulin different from the immunoglobulin of the immunized cell, so as to contaminate the monoclonal antibody composition. Another consideration is the efficiency with which the fusion may be performed. That is, the number of viable hybridomas which are produced per $10^5$ human lymphocytes employed in the fusion.

Additional considerations include the nature of the required nutrient medium. The nutrient medium is important for a number of reasons. First, fetal calf serum is in short supply and has become extremely expensive. Therefore, it presents a serious deterrent to commercial production of human monoclonal antibodies. Secondly, because of the spectrum of materials present in fetal calf serum, separation and purification of the human monoclonal antibodies is complicated.

Therefore, while human monoclonal antibodies can now be prepared to a wide variety of haptens and antigens, there will still need to be substantial improvements. These improvements will involve the fusion partners and the manner in which the human monoclonal antibodies are prepared, particularly where the use of the monoclonal antibodies are for therapeutic purposes.

2. Description of the Prior Art

Olsson and Kaplan, Proc. Nat'l. Acad. Sci. U.S.A. 77, 5429–5431 (1980), describe the establishment of a continuous culture of purely allogenic human hybridomas secreting specific human antibody having myeloma cells as the fusion partner. Nowinski et al., Science, 210, 537–539 (1980), describe the isolation of a mouse-human hybridoma secreting a human monoclonal antibody against Forssman antigen. Croce et al., Nature, 288, 488–489 (1980), describe the production of human antibodies from a hybridoma using as a fusion partner a HPRT-deficient human B-cell line. The fusion partner was crossed with peripheral lymphocytes and secreted human IgM specific for measles virus nucleocapsids. Royston et al., Manuscript in Press and patent application Ser. No. 247,652 disclose the isolation and use of a human B-lymphoblastoid cell line as a fusion partner, the cell line is referred to as UC 729.

SUMMARY OF THE INVENTION

Improved fusion partners are provided for crossing with lymphoid cells for the production of hybridomas capable of secreting human monoclonal antibodies. A human lymphoblastoid B-cell line is grown and selected for high fusion efficiency with lymphoid cells and ability to grow in serum-free nutrient medium. The resulting fusion partner can be fused with a wide variety of lymphoid cells to produce human monoclonal antibodies for diagnostic and therapeutic purposes.

DESCRIPTION OF THE SPECIFIC EMBODIMENTS

A human lymphoblastoid B-cell line is provided as a fusion partner for generating immunoglobulin secreting human-human hybridomas. The subject cell line is characterized by being derived from the human lymphoblastoid B-cell line (B-LCL) designated as UC 729-6, which in turn was derived from the cell line WI-L2.

The subject cell line is an Epstein-Barr virus transformed cell, is hypoxanthine phosphoribosyl transferase (HPRT) type deficient (6-thioguanine resistant) and expresses IgM with kappa light chains on both the surface and in the cytoplasm. Supernatants from the cell line are negative for IgA, IgD, IgG, and IgM.

The subject cell line will be referred to as WI-L2-729HF$_2$. The subject cell line provides enhanced fusion efficiency over the parent cell line. The subject cell line was obtained by transferring the parent cell line from a nutrient medium comprising RPMI 1640 plus decreasing amounts of fetal calf serum into Iscove's modified serum-free medium (Iscove and Melchers, (1978) J. Exp. Med. 147, 923–933) conditioned with peritoneal fibroblasts and plated over a period of about two months at relatively high densities of the order of about $5 \times 10^6$ cells per ml. Following the high density platings, the cells were cloned to limiting dilutions in Iscove's conditioned medium containing insulin and approximately 900 clones were analyzed for fusion frequencies over the period of the next six months. Out of this, one cell line, HF$_2$ had a fusion frequency of about 2-5 fusions per $10^5$ human lymphocytes and this cell line was expanded in Iscove's serum-free medium to provide the subject cell line.

The WI-L2 cell line is described in Levy et al., Cancer, 22, 517–524 (1968); and Levy et al., J. Natl. Cancer Instit., 46, 647 (1971).

For production of monoclonal antibodies, the subject cell line is fused with human lymphoid cells immunized against a haptenic or antigenic determinant. Various sources of lymphoid cells may be employed. Spleen cells can be used, which are immunized in vivo or in vitro.

When in vivo immunization is involved, the host is immunized at least once, usually at least about two weeks prior to a splenectomy. After freeing a single cell suspension of the spleen tissue of red blood cells and granulocytes, the viable mononuclear cells are suspended in an appropriate nutrient medium and nonadherent cells separated from the adherent cells. The resultant lymphoid cell culture may then be fused with the subject cell line.

For in vitro immunization, a single cell suspension of spleen cells is prepared, and viable cells isolated and seeded in a nutrient medium, which includes the immunogen at an appropriate concentration. After sufficient time for immunization to occur, the viable cells are isolated and used for fusion. Instead of spleen lymphoid cells, lymphocytes isolated from peripheral blood may be employed. To immunize the lymphocytes, the lymphocytes are combined in an appropriate nutrient medium containing macrophages and immunogen to prime the lymphocytes. After sufficient time for priming, usually two to four days, the viable cells are isolated and employed for fusion.

Isolation of lymphocyte cells can be achieved with Ficoll-Hypaque gradient centrifugation and the viable cells grown in nutrient medium, containing about 15% FCS, about 40 $\mu$g/ml antigen and about $10^5$ macrophages/ml and the cells incubated for about three days to prime the cells and produce blast cells. The viable cells may then be used for fusion.

Fusion can be readily achieved in accordance with known techniques. Desirably, the Kohler and Milstein technique, as modified by Gefter et al., Somat. Cell Genet., 3, 231–236 (1977) is employed. The method employs a relatively high concentration of polyethylene glycol with an excess, usually at least a 2 to 1 ratio, of lymphoid cells to the subject cell fusion partner. The time for the fusion is generally under about 8 minutes and the resulting cells rapidly washed of the non-ionic detergent. The subject cell concentration will generally be about $10^6$ to $10^9$ cells/ml with the lymphoid cell concentration being from about 2 to 3 times its fusion partner.

The cells are then seeded at relatively high concentrations in microplates on human foreskin feeder layers and grown in an appropriate nutrient medium containing standard HAT components. Littlefield, Science 145, 709–710 (1964). After culturing for a sufficient time, usually in excess of about 4 weeks, the hybridomas appear, with the absence of growth of the parent cells.

The supernatants of the resulting hybridomas are then monitored for immunoglobulin production. Conveniently, antibodies to the chain type can be used for assaying for the presence of immunoglobulin. Radioimmunoassays, nephelometric techniques, and the like may be employed.

Once positive wells are detected, the cells in the positive wells may be cloned under limiting dilution conditions. The resulting clones are then expanded and the monoclonal antibodies harvested in accordance with known procedures. The monoclonal antibodies may be freed of other proteins in accordance with known techniques, such as electrophoresis, chromatography, or the like.

Monoclonal Antibodies

In referring to monoclonal antibodies, it is intended to include not only IgM, but also IgG, IgD, IgE and IgA. Antibodies may be produced against any haptenic or antigenic compound of which there is an ever increasing number which have been involved in immunization. Illustrative haptenic compounds of interest, but clearly not exhaustive, are drugs, both naturally occurring and synthetic, such as opioids, amphetamines, barbiturates, steroids, catecholamines, dilantin, theophylline, histamine, PCP, cannabinoids, valproate, digoxin, and the like. Antigens of interest include a wide variety of hormones and other physiologically active proteins, histocompatability antigens, pathogen surface antigens, viral antigens, toxins, allergens, and the like.

For a more complete list of ligands of interest for use in diagnostics or for therapy, see U.S. Pat. No. 4,193,983, particularly Col. 7–11, inclusive, which disclosure is incorporated herein by reference.

The monoclonal antibodies of the subject invention are homogeneous in the sense that the variable regions for the antibodies are constant. That is, better than about 90% of the antibodies are the same composition in the variable region, usually better than 95%. Normally, the immunoglobulin will have less than about 1 mole % of antibodies having chains of a different type from the dominant component.

By having a uniform composition of immunoglobulins, many advantages ensue. First, one is ensured of freedom from immunoglobulins specific for other than the predefined antigen. The presence of undesired immunoglobulins is disadvantageous for analytical work as well as for therapeutic purposes. Secondly, one is assured of a single binding site, as compared to antibody compositions obtained from myeloma patients. Third, one can obtain an exact titer for a specific determinant site, rather than averaging over the entire composition. With analytes, better control of cross-reactivities can be achieved with a homogeneous composition.

The subject human monoclonal antibodies can find use as antigens, either for the entire molecule or for the individual, L, H and J chains, or portions thereof, such as the variable and hypervariable regions. The antibodies may also be used as standards for assaying for the various types of immunoglobulins. The immunoglobulins, because of their homogeneity, can be used for sequencing to provide the genetic sequence for preparation of probes e.g. radioactively labeled DNA, isolation of the genes from the genome, or synthesis of genes or a portion thereof.

The subject human monoclonal antibodies find use in conventional applications for antibodies, such as immunoassays, cell sorting, electrophoretic analysis, histology, cytology and the like. Besides the conventional uses, the subject monoclonal human antibodies have additional uses since they are allogenic (another member of the same species) proteins and should not be immunogenic to a human host.

Because the human monoclonal antibodies should be acceptable to the human immune system, the monoclonal human antibodies can be used for induction of passive immunity. Among immune sera which are presently available are antisera for tetanus, hepatitis, vaccinia, mumps, rabies, pertussis, botulism, gas gangrene, varicella, as well as other diseases.

The antisera are normally administered parenterally or by ingestion in dosages varying from 100 to 20,000 units, or in amounts based on immune serum of 0.005 to 1 ml/kg of the host. (Medical Pharmacology 6th ed. Edited by Meyers, Jaivetz and Goldfien, Lange Medical Publications, 1978, pages 612–615.) Particular dosages will vary depending upon the manner of administration. Various carriers or media can be used, such as physiological saline, capsules, plasma, or the like. Other additives may also be included, such as stabilizers, drugs, proteins, and the like.

The human monoclonal antibodies can also be used for site directed therapy. By preparing antibodies recognizing determinant sites of an organ, abnormal cell e.g. tumor, or infectious cell, the antibody can serve to direct a drug or other therapeutic means to such site and maintain such drug or therapeutic means at such site. For example, the antibodies can be attached to slow release particles containing a particular drug for treatment of an infection. The antibodies would bind to the infected site, maintaining a high localized concentration of the drug in the infected area.

Other uses include diagnosis, where the antibodies would be radioactively labeled, providing for localization of the radioactive label at a particular site, permitting radiography at a particular organ or other internal site.

The hybridomas can also serve as a concentrated source of messenger RNA or as a source of the genes for the light and heavy chains of immunoglobulins e.g. IgM and IgG.

The following examples are offered by way of illustration and not by way of limitation.

EXPERIMENTAL

A HAT-medium sensitive mutant cell line was obtained by subjecting the known human lymphoblastoid B-cell line WI-L2 to increasing concentrations of 6-thioguanine and isolating mutants resistant to 6-thioguanine. A thioguanine-resistant clone was isolated and designated UC 729-6. The UC 729-6 cells are routinely grown in RPMI 1640 media supplemented with 10% FCS, 2mM glutamine and $10^{-4}$M 6-thioguanine. UC 729-6 doubles in concentration every 17 hours.

The above cells were then grown at very high densities, approximately $1-1.5\times11^7$ cell/ml and at this high confluent density, the cells were shifted slowly into ever-decreasing concentrations of fetal calf serum. The concentration of fetal calf serum was decreased by 2% each week from the original 15% and the cells were seeded at high densities i.e. $5\times10^6$ cells per transfer. Following four months of successive transfers, the cells grew on 2% FCS in Iscove's synthetic medium (Iscove and Melchers, supra), but not in Iscove's synthetic medium by itself.

Iscove's media was conditioned with growing mouse peritoneal fibroblasts in the presence of about 10 $\mu$g/ml insulin. Monolayers of mouse fibroblasts in their second or third doubling (in some cases as much as five doublings, but not greater), were incubated with Iscove's synthetic media for 24 hours. This conditioned media was then used 50—50 with normal Iscove's media to shift the modified 729 cells into serum-free conditions. Out of about 50 flasks of cells, one flask developed qualities that would grow in Iscove's serum-free media and that cell line was continued. These cells showed no improvement in fusion frequency.

These cells were cloned out to limiting dilutions so that each population was an expansion of a single cell. Each of these populations (approximately 900) were grown into colonies of approximately $5\times10^7$ cells and these cells were fused with human lymphocytes in a procedure using polyethylene glycol 1000 elevated to pH8.2 and containing 15% dimethylsulfoxide and incubated at 27° C. for 8.5 minutes. Following the fusion, these cells were screened for fusion events where lymphocytes had fused to the fusion partner and each of some 900 colonies were scored for their fusion frequencies. One of these colonies showed drastically increased fusion efficiency and frequency and that colony was expanded into the cell line which is now termed 729-HF$_2$. The fusion frequency of this cell line is approximately 5 fusions per $10^5$ lymphocytes present and represents a 3 log fold increase in fusion efficiency. The cell line was also shown to be HGPRT negative. Furthermore, the subject cell line can fuse with human lymphocytes that have been immunized in vitro.

The clone is maintained in modified Iscove's serum-free medium at a minimum cell density of $1\times10^3$/ml and a maximum density of $5\times10^6$/ml. When allowed to grow to densities greater than about $5\times10^6$ cell/ml, these cells revert to the earlier lower fusion frequency and require recloning and selection for higher fusion frequencies. Fusion frequencies are greater if the cells are harvested for fusion at densities between $1\times10^3$ and $3\times10^6$/ml.

Fresh human tonsilar lymphocytes were dissociated and prepared as described by Lundak et al., J. Immunol. Methods, 20, 277 (1979), and cultured in modified human serum medium as described by Fauci and Prat, J. Exp. Med., 44, 674 (1976). Each culture of $1.1\times10^7$ lymphocytes was immunized with 30 $\mu$L of a 1% sheep erythrocyte suspension and incubated at 37° C. with 5% CO$_2$ for various periods of time before fusion.

Immunized lymphocytes were harvested from culture described above at 24 hour intervals, with the 96 hour immunized cultures providing lymphocytes which fused to produce immunoglobulin secreting hybrids. These lymphocytes were washed once with RPMI1640 and adjusted to $1\times10^8$ cells per fusion in RPMI1640. The subject clone cells were harvested from culture when their density was between $1\times10^6$/ml and $2\times10^6$/ml, washed in RPMI1640 and added to the immunized lymphocytes at a ratio of 10 lymphocytes to 1 fusion partner. Fusions were conducted as described previously (Kohler and Milstein, Eur. J. Immunol. 6, 511, 1976), using polyethylene glycol 1000 at pH7.2, RPMI1640 with 15% DMSO and incubated at 27° C. for 8.5 minutes. Following each fusion the cell suspension was resuspended in 50ml RPMI1640 containing 20% FCS and dispensed in 1 ml aliquots into 2 cm$^2$ wells containing $1\times10^4$ human thymus fibroblast cells in their fifth doubling. To these cultures 1 ml of HAT medium was added by dilution daily for 14 days and then on alternate days 1 ml of RPMI1640 with 20% FCS was added in addition to the wells. Hybrids began to grow after 21–38 days in culture. HAT resistant clones were cloned to limiting dilution in Iscove's modified serum-free medium previously conditioned by 24 hour growth of the subject fusion partner cells ($1\times10^6$/ml). Hybrid supernatants were examined for human immunoglobulin content by hemagglutination inhibition and Elisa (Engvall and Perlmann, J. Immunol. 109, 129, 1974) employing peroxidase conjugated polyvalent goat antihuman immunoglobulins G, M, and A.

Two clones HH09A3 and HH09A2 were characterized. While the original cell line WI-L2-729HF was karyotyped and found to be 2N male, the above clones karyotyped at 5 weeks post fusion were found to be 4N. The hybrid cells were maintained at subconfluent levels and were fed twice weekly. Seven weeks post fusion, both hybrid cell lines were cultured in HAT medium for one week, and modal chromosome numbers were determined in the ninth week post fusion. Both lines demonstrated chromosome loss with time and stabilized at a modal chromosome number of 62.

Hybrid cell lines HH09A3 and HH09A2 were expanded in Iscove's modified media and the culture supernatants characterized for antibody specifity. Fresh sheep erythrocytes were incubated in supernatants for 1 hour at room temperature, washed twice and incubated with fluorescein conjugated heavy and light chain specific goat anti-human immunoglobulin antibody for 1 hour at 37° C., washed twice and observed under fluorescence microscopy. Antibody from HH09A3 specifically reacted with all sheep erythrocytes and HH09A2 reacted with 48% of the red cells. Absorption for 1 hour with a one-fourth volume of sheep erythrocytes removed all of the antibody from the supernatants. Ox and horse erythrocytes did not bind the supernatant antibodies and were unable to absorb the antibody activity from either supernatant.

Sheep erythrocytes were incubated with the above mentioned supernatants, washed three times and incubated for one hour with sheep erythrocyte absorbed goat anti-human heavy chain $\gamma$, $\mu$ and $\alpha$ specific and $\kappa$ and $\lambda$ chain specific antibody. The erythrocytes were washed and polyvalent rabbit anti-goat immunoglobulin was added and fluorescence as well as the amount of hemagglutination recorded. Supernatant HH09A3 contains IgG$\kappa$ light chain antibody molecules and HH09A2 contain IgA$\kappa$ light chain antibody molecules. Immunoglobulin subclass was determined for IgG containing supernatants from clone HH09A3 and IgA containing supernatants from clone HH09A2 as well as supernatants from $1\times10^8$ sonicated WI-L2-729HF cells in log growth phase using the hemagglutination inhibition assay. (Goodson, J. Immunol. Methods, 37, 89, 1980).

Supernatants from HH09A3 contain $\gamma2$ heavy chain as does the WI-L2-729HF sonicated cell supernatant. Supernatant HH09A2 contains $\alpha1$ heavy chains while the WI-L2-729HF supernatants did not contain detectable IgA heavy chains.

Supernatants from 24 hour cultures of $5\times10^5$ cells from clones HH09A3 and HH09A2 were assayed for immunoglobulin levels 7, 12 and 20 weeks post fusion by a double antibody radioimmunoassay. (Yunginger and Gleich, J. Allergy Clin. Immunol. 50, 362, 1972). Both the IgA and IgG secreting hybridoma lines continue to produce moderate levels of sheep erythrocyte antibody for 20 weeks post sheep erythrocyte fusion. The parent fusion partner does not secrete detectable IgA and only very small IgG into the supernatant.

The subject fusion partner WI-L2-729HF cells have high frequency of fusion and therefore provide efficient fusion partners. Upon hybridization with immunized lymphocytes, the resulting hybrids may be cloned and produce moderate amounts of specific immunoglobulin for extended periods of time. Therefore, the subject fusion partners provide for efficient production of hybridomas for producing human monoclonal antibodies to the varying types of immunoglobulins, such as IgA, IgD, IgE, IgG and IgM.

Although the foregoing invention has been described in some detail by way of illustration and example for purposes of clarity of understanding, it will be obvious that certain changes and modifications may be practiced within the scope of the appended claims.

What is claimed is:

1. An immortal B-cell line WI-L2-729HF$_2$.
2. A hybridoma resulting from the fusion of an immunized lymphocyte and a cell line according to claim 1.

* * * * *